United States Patent [19]

Müller

[11] Patent Number: 4,939,177

[45] Date of Patent: Jul. 3, 1990

[54] USE OF AVAROL FOR THE CONTROL OF AIDS AND ARC

[75] Inventor: Werner E. G. Müller, Wiesbaden-Biebrich, Fed. Rep. of Germany

[73] Assignee: Merz + Co. GmbH & Co., Frankfurt am Main, Fed. Rep. of Germany

[21] Appl. No.: 58,200

[22] Filed: Jun. 4, 1987

Related U.S. Application Data

[63] Continuation-in-part of Ser. No. 820,440, Jan. 17, 1986.

[30] Foreign Application Priority Data

Jun. 7, 1986 [DE] Fed. Rep. of Germany ....... 3619202

[51] Int. Cl.$^5$ .............................................. A61V 31/045
[52] U.S. Cl. .................................................... 514/729
[58] Field of Search ....................................... 514/729

*Primary Examiner*—Jerome D. Goldberg
*Attorney, Agent, or Firm*—Gordon W. Hueschen

[57] ABSTRACT

The invention concerns the use of avarol and its derivatives and pharmaceutical compositions thereof for the control of AIDS and AIDS-related Complex (ARC).

2 Claims, No Drawings

USE OF AVAROL FOR THE CONTROL OF AIDS AND ARC

This application is a continuation-in-part of prior-filed copending application Ser. No. 820,440, filed Jan. 17, 1986, presently still pending.

The present invention relates to the use of avarol and derivatives thereof for the control of AIDS and ARC.

Avarone and its hydroquinone derivative (avarol) are natural substances which are present in the marine sponge *Dysidea avara*. Federal Republic of Germany OS 34 27 383, published Jan. 30, 1986, describes that avarone and avarol and its derivatives have antitumoral, antibacterial and antimycotic properties which make them appear suitable, in particular, for the treatment of cancer and infectious diseases. Furthermore, it is stated therein that these compounds have a certain virostatic action in vitro against cultures of herpes simplex virus and therefore against DNA viruses. However, no data has been heretofore available concerning the possible inhibition of RNA viruses.

In addition to this, it has been found that avarone and its derivatives have antimutagenic activity. Finally, it has been discovered that avarone and its derivatives also have an antileukemic action. The existence of this antileukemic action has been derived from studies in vitro as well as in vivo with mouse leukemia cells L5178-Y. Up to the present time, however, no virus causality in the case of tumors is known on the part of these leukemia cells. Therefore, it was not obvious to use avarol or the derivatives thereof for the control of the virus-produced clinical picture of AIDS.

The object of the present invention is to provide a promising method of controlling AIDS or AIDS-related complex (ARC).

AIDS is caused by the human T-cell leukemia/lymphotropic virus of type III (HTLV-III), which is also known as lymphadenopathy-associated virus (LAV). HTLV-III belongs to the type of RNA viruses which differ in essential points from the DNA viruses. The viral attack is the main cause of a spectrum of immunological disturbances of which AIDS manifests itself clinically most severely in the form of Karposi's sarcoma or of AIDS-Related Complex (ARC). Up to now, no effective therapeutic treatment of AIDS or ARC has been possible.

It has been surprisingly now found that avarol and its derivatives are excellently suited for controlling acquired immunodeficiency syndrome (AIDS) or AIDS-Related Complex (ARC).

The object of the invention therefore is the use of avarol and its derivatives of the general formula (Ib):

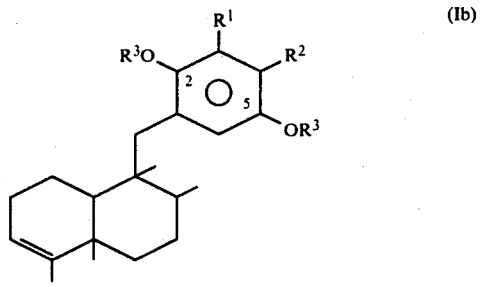

and the 3,4-dihydro derivative thereof, in which formulas $R^1$ and $R^2$ represent, independently of each other, a hydrogen atom, or a $C_1$–$C_4$ alkylamino group, $R^3$ is a hydrogen atom, a $C_1$–$C_4$ alkyl group, or a $C_2$–$C_6$ acyl group, or a physiologically easily hydrolyzable ether or ester group, or both $R^3$ groups together stand for a $C_4$–$C_6$ diacyl group, and the physiologically compatible salts thereof, or a mixture of said compounds, for the control of AIDS and ARC.

Of the above-indicated compounds, avarol (formula Ib: $R^1=R^2=R^3=H$) is preferably used. In the compounds of formula (Ib) both moieties $R^1$ and $R^2$ are preferably a hydrogen atom.

The compounds of formula (Ib), which may contain amino groups, can be used as acid addition salts. There are concerned here salts with ordinary physiologically compatible inorganic or organic acids such as hydrochloric acid, sulfuric acid, phosphoric acid, tartaric acid, lactic acid, maleic acid and the like.

The compounds of formula (Ib) in which $R^3$ stands for H can also be used as salts with ordinary physiologically compatible inorganic or organic bases such as sodium hydroxide, alkylamine, hydroxyalkylamines, and the like.

Physiologically easily hydrolyzable esters and ethers of avarol and the compounds of formula (Ib) in which $R^3=H$ can easily hydrolyze enzymatically or chemically in the body to the corresponding hydroquinone compounds. Suitable esters are, for example, the orthoformate acid ester, esters of alpha-ketocarboxylic acids, for instance, pyruvic acid, toluene sulfonic acid esters and the like. Suitable ethers are, for instance, methoxymethylether, tetrahydropyranylether, and the like.

The preparation of avarol is described in Federal Republic of Germany OS 34 27 383. For this the marine sponge *Dysidea avara* is extracted with ethyl acetate. Avarol is recovered from the extract by column chromatography on silica gel.

The derivatives of general formula (Ib) are prepared by reacting avarol or its alkylamino derivatives which are protected at the amino group with a $C_2$–$C_6$ acyl chloride or with a corresponding carboxylic anhydride. As acyl chlorides use may be made, for instance, of straight-chain acyl chlorides, such as acetyl-, propionyl-, n-butyryl-, n-valeroyl-, and capronoyl chloride, as well as branched-chain acyl chlorides, such as isobutyryl-, isovaleroyl-, 2-methylbutyryl- and trimethylacetyl chloride. As suitable acid anhydrides there enter into consideration, for instance, straight-chain acid anhydrides such as acetanhydride, propionic anhydride, butyric anhydride, valeric anhydride, and other carboxylic acid anhydrides, as well as branched-chain acid anhydrides such as isobutyric anhydride, isovaleric anhydride, 2-methylbutyric anhydride and trimethylacetanhydride. When a $C_4$–$C_6$-dicarboxylic acid chloride or an anhydride of a $C_4$–$C_6$ dicarboxylic acid is used, the cyclic esters of formula (Ib) are obtained.

The compounds of formula (Ib) are preferably reacted with the acyl chlorides or carboxylic acid anhydrides in the presence of pyridine (S. de Rosa, L. Minale, R. Riccio and G. Sodano, J. Chem. Soc. Perkin I. 1976, 1408–1414; *Organikum*, VEB Deutscher Verlag der Wissenschaften, 13th edition, Berlin 1974, pages 441–446).

The $C_1$–$C_4$ alkyl ethers of avarol and the compounds (Ib) can be prepared by reacting the hydroquinone compound, preferably in the form of the Na or K salt thereof, with the corresponding $C_1$-$C_4$ alkyl halide or di-$C_1$-$C_4$-alkylsulfate.

The compounds which are to be used in accordance with the invention are generally employed in the form of pharmaceutical compositions which are produced in the form of dosage units and can be administered systemically, i.e., orally, rectally, or parenterally (intramuscular, intravenous and subcutaneous).

The compositions contain at least one compound of general formula (Ib) or a physiologically compatible salt thereof in an amount effective for the treatment, elimination, alleviation, or improvement of AIDS or ARC or in an immunity-defect eliminating amount, possibly together with a pharmaceutically compatible excipient and/or adjuvant. Such pharmaceutical agents contain, for instance, 0.5 to 98 wt% of at least one compound of the invention, together with a pharmaceutical excipient.

If the agent is present in the form of a dosage unit, it preferably contains 10 to 100 mg of the compound used in accordance with the invention.

The pharmaceutical agents can be present, for oral administration in solid form, for instance, as tablets, pastilles, capsules or powder, or in liquid form, for instance, as aqueous or oil suspensions, syrup, elixir, solution or liquid-filled capsules.

Preferred oral agents are in the form of tablets or capsules and can contain ordinary excipients such as binders (for instance, syrup, acacia, gelatin, sorbitol, tragacanth or polyvinylpyrrolidone), fillers (for instance, lactose, sugar, corn starch, potato starch, calcium phosphate, sorbitol or glycine), lubricants (for instance, magnesium stearate, talc, polyethylene glycol or silica), disintegration agents (for instance, starch) and wetting agents (for instance, sodium lauryl sulfate).

Agents for parenteral administration are in general in the form of a solution or suspension of the compounds used in accordance with the invention together with ordinary pharmaceutical excipients, for instance, in the form of an aqueous solution for intravenous injection or of an oil suspension for intramuscular injection. Agents suitable for parenteral administration are obtained by dissolving 0.1 to 10 wt% of the compound of the invention in water or an excipient which consists of an aliphatic polyalcohol such as glycerin, propylene glycol or polyethylene glycols or mixtures thereof. The polyethylene glycols consist of a mixture of non-volatile, ordinarily liquid polyethylene glycols which are soluble both in water and in organic liquids and the molecular weights of which range from 200 to 1500.

Pharmaceutical agents for rectal administration are in the form of suppositories, the compounds of the invention being incorporated in a suitable suppository base such as cocoa butter, hydrogenated fats, polywaxes or polyethylene glycols, in an amount of 1 to 10% by weight.

The pharmaceutical agents are prepared by ordinary methods, for instance, by tabletting, incorporating of the compounds used in accordance with the invention in a suppository base, sterile filtration and filling in ampules or dropper bottles of a solution of the compounds used in accordance with the invention in water for injection together with ordinary additives such as sodium chloride, sodium dihydrogenphosphate, disodium edetate (ethylene diaminotetraacetic acid disodium salt), benzyl alcohol or sodium hydroxide in order to adjust the pH.

The procedure for the treatment of AIDS or ARC comprises the administration of a therapeutically (antivirally or immunomodulating or prophylactically) active amount of avarol or a derivative thereof or mixtures thereof or of a pharmaceutically-compatible salt thereof to a patient who requires this treatment.

The dose depends primarily on the specific form of administration and the purpose of the therapy. The size of the individual doses as well as the program for administration can be determined best on basis of a doctor, in which connection the age, weight and condition of the patient, the route of administration and the nature and severity of the illness must be taken into account. In general, the daily dose is 2 to 20 mg/kg of body weight and preferably 3 to 10 and particularly 6 to 7.

The duration of the treatment depends on the nature and severity of the disease. It extends in general over several weeks, for instance, 4 to 8 weeks.

The compounds to be used in accordance with the present invention act in a diversified manner against human T-cell leukemia virus of type III (HTLV-III) and they produce a stimulating action on the immune system so that the endogenous defense forces against AIDS, AIDS-related complex (ARC) and related illnesses are reinforced. These compounds can therefore be used for the therapeutic and prophylactic treatment of the diseases caused by the AIDS virus.

The activity of the compounds used in accordance with the invention will be examined below on basis of pharmacological in-vitro test systems using avarone and avarol as example.

For this, the H9 cell line was used, it consisting of a cloned OKT4+ T-cell line in which the AIDS virus propagates (M. Popovic, M. G. Sarngadharan, E. Reed and R. C. Gallo; Science 224, 497–500 (1984)).

Test Procedure

Purification of HTLV-III reverse transcriptase and assay conditions:

The HTLV-III reverse transcriptase used for the present experiments (prepared by the method of P. S. Sarin, Y. Taguchi, D. Jun, A. Thornton, R. C. Gallo, B. Oeberg, Biochem. Pharmacol. 34, 1985, pages 4075 to 4079) was purified by sequential chromatography on DEAE-cellulose, phosphocellulose and hydroxyapatite. The purified enzyme was stored in 50 mM tris-HCl (trishydroxymethylaminomethane) (pH 7.5), 1 mM dithiothreitol (DTT), 0.01% Triton X-100 and 20% glycerin. The assays for reverse transcriptase were carried out in a reaction mixture (50 $\mu$l) which contained 50 mM tris-HCl (pH 7.5), 5 mM DTT, 10 mM $MgCl_2$, 100 mM potassium chloride, 0.01% Triton X-100 ($C_8H_{17}$-$C_6H_4$-$(OCH_2CH_2)_{9\text{-}10}$-OH) or NP40 (non-ionic detergent Nonidet P 40, brand name of the Sigma company, i.e., octylphenol ethylene oxide condensate), 10 $\mu$g/ml $(dT)_{15}.(A)_n$ (hybrid polymers of the oligo- or polynucleotides oligodeoxythymidylic acid and polyadenylic acid) as template primer and [$^3$H]-deoxythymidine triphosphate ([$^3$H]-dTTP). The reaction mixture was incubated for one hour at 37° C. and the reaction was stopped by adding 50 $\mu$g of yeast-tRNA and 2 ml of a 10% trichloroacetic-acid solution (TCA) containing 1 mM of sodium pyrophosphate. The samples were filtered through a millipore filter (0.45 $\mu$m), and washed, first with 5% TCA-solution (5×) and then with 2 ml of 70% ethanol. The filters were dried under a heating lamp, whereupon scintillation liquid was added and the radioactivity was determined in a beta-scintillation counter.

HTLV-III Infection of H9-cells

H9-cells (M. Popovic, M. G. Sarngadharan, E. Reed, R. C. Gallo, Science: 224, 1984, 497–500) were treated with Polybren ® (hexadimethrinbromide available on the market; 2 μg/ml) for 30 minutes at 37° C., washed free of Polybren and infected with $2 \times 10^8$ HTLV-III virus particles (isolated from H9 cell cultures by the method of M. Popovic; see above) per $4 \times 10^5$ H9 cells. Some assays which were not treated with drugs were used as positive controls, while different concentrations of the compound to be tested (avarone or avarol and their derivatives) were added to the test samples. The HTLV-III reverse transcriptase activity of these cultures was analyzed in the manner described above.

Immunofluorescence Assay

The immunofluorescence assays were carried out on methanol:acetone (1:1)-fixed cells with the use of monoclonal antibodies (from the mouse) against HTLV-III p15 (core protein of MW=15,000) and p24 (core protein of MW=24,000). Both of these proteins are marker proteins which indicate the presence of virus particles in the cells. The HTLV-III Infected cells with or without drug treatment were fixed on toxoplasmosis slides. After fixation with methanol-acetone (1:1) for 30 minutes at room temperature, the slides were stored in sealed plastic containers at −20° C. until use. The monoclonal antibodies were added to the cells, incubated at room temperature in a moisture chamber for one hour and washed for two hours with PBS (phospate buffered saline) containing 0.25% Triton X-100. The cells were then treated for one hour with fluorescein (FITC) labeled goat anti-mouse IgG (Capell Labs.) and washed overnight with PBS buffer containing 0.25% Triton X-100. Fifty percent glycerin was added to the slides and the cell fluorescence was determined with a Zeiss fluorescence microscope.

1. Cell Growth

H9-cells as well as H9-cells infected with HTLV-III were used in a concentration of $0.2 \times 10^6$ cells/ml of culture medium for the inoculating of a culture medium. After incubation for four days, the density of the H9-cells was $1.3 \times 10^6$ cells/ml, while the density of the H9-cells infected with HTLV-III was only $0.5 \times 10^6$ cells/ml; these two values formed the control values.

Thereupon samples of H9-HTLV-III cells, $0.2 \times 10^6$ cells/ml, were treated for four days with different concentrations of avarol. The following results were obtained:

| | Concentration of the drug (μg/ml) | Cell Concentration $\times 10^6$/ml |
|---|---|---|
| Control-infected cells | 0 | 0.5 |
| Avarol (infected cells) | 0.1 | 1.42 |
| | 1 | 1.09 |
| Control-uninfected | 0 | 1.3 |

It is clear that avarol in the concentrations of about 0.01 μg/ml increase the growth rate of H9-HTLV-III cells to values which lie within the range of the control, namely of the H9-cells without HTLV-III.

2. Inhibition of the Production of Reverse Transcriptase by H9-HTLV-III cells which were treated with avarol It was examined whether the four-day addition of avarol to H9-HTLV-III cells stops the production of HTLV-III viruses. Reverse transcriptase was selected as measure for the amount of virus in the culture medium. Therefore, inhibition of the reverse transcriptase indicates inhibition of the production of virus. The results are set forth in the following table:

| Compound added | Concentration of the compound (μg/ml) | Reverse Transcriptase activity (in %) |
|---|---|---|
| None | — | 100 |
| Avarol | 0.1 | 36 |
| | 1 | 20 |
| | 5 | 18 |

It is clear that, in the supernatant of the H9-HTLV-III cells which were not treated with avarol, a considerable activity of reverse transcriptase was indicated. The addition of avarol led to a dose-dependent reduction of the reverse transcriptase activity in the supernatant. Even with a very low dose of 0.1 μg/ml, a considerable inhibition was noted. The compounds used in accordance with the invention are therefore able to inhibit virus replication practically completely at doses in which various in vitro parameters, for instance, cell growth, are practically not detrimentally affected.

3. Inhibition of HTLV-III p15 and p24 expression in H9-HTLV-III by avarol

It was found that avarol possess a strongly inhibitory action on the expression of HTLV-III p24 and p15 in infected H9-cells. When the target H9-cells were treated with the HTLV-III isolate and cultivated without the compounds to be tested, the H9-cells were infected and, as established by indirect immunofluorescence assay, there was expression of the p24 and p15 protein. After incubation of the H9-HTLV-III cells with the compounds to be tested, a practically complete protective effect was observed. The following results were obtained:

| Compound added | Concentration of the compound (μg/ml) | Expression of p15 and p24 (in %) | |
|---|---|---|---|
| | | p15 | p24 |
| None | — | 100 | 100 |
| Avarol | 0.1 | 37 | 28 |
| | 1 | 12 | 14 |
| | 5 | 12 | 14 |

It is clear that avarol causes a significant reduction in the expression of the HTLV-III proteins p15 and p24.

Toxicity

The in-vivo toxicity (mg compound/kg) of avarol in male NMRI mice is as follows:

Acute toxicity: $LD_{50}$ 269.1, $LD_{10}$ 156.4

Subacute toxicity: $LD_{50}$ 218.4, $LD_{10}$ 138.6 (Müller et al., Cancer Research 1985, 45, 4822–4826).

IDENTITY

The active antiviral and antitumor ingredients or agents of the present invention have the formulas:

Avarol

2-[(1R)-1,2,3,4,4a,7,8,8aα-octahydro-1β,2β,4aβ,5-tetramethyl-1-naphthylmethyl]-1,4-benzenediol

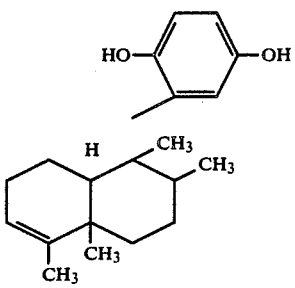

The compound 3,4-dihydroavarol is known from L. Minale et al., Tetrahedron Letters 36, 3401–3404 (1974) and Müller et al., Cancer Research 45, 4822–4826 (1985).

PRODRUGS OR PRECURSORS AND THEIR PREPARATION

The compound avarol and its 3,4-dihydro derivatives may also be employed or embodied in pharmaceutical compositions according to the invention and administered in the form of compounds which convert or metabolize thereto after introduction into the living animal body. Such compounds are commonly referred to today as prodrugs or precursors, and representative examples include their esters and alkylamino derivatives. As already indicated, some of these compounds are known in the prior art, whereas others are made in a known manner corresponding thereto. Representative of such prodrugs and precursors, and their preparation, are set forth in the foregoing and in the following.

The following Examples serve to explain the invention, but are not to be construed as limiting.

EXAMPLE 1

Avarone and avarol 3 kg of fresh sponge (water containing) are crushed in a Starmix ™ mixer and extracted with 250 ml of ethyl acetate; the extract thus obtained is dried over magnesium sulfate and then filtered. The filtrate is concentrated to dryness. The remaining residue (about 50 g) is taken up in about 100 ml of benzene and chromatographed over a silica-gel column (about 200 g) with benzene as eluent. Avarone appears in the eluate while avarol remains in the column. Avarol is eluted with a mixture of benzene and ethyl acetate (90:10, V:V). The eluate is concentrated to dryness and avarol then obtained in pure form by crystallization from dichloromethane-acetone. Avarone is purified by recrystallization from benzene. Yield: 0.7 g avarone; 8.9 g avarol; avarone MP: 62°–64° C.; avarol MP: 148°–150° C.

EXAMPLE 2

Avarol diacetate (a) 500 mg of avarol are dissolved in 20 ml of absolute pyridine and 1 g of acetyl chloride is added in individual portions to the solution, while shaking. The solution is worked up in the customary manner, concentrated to dryness, and the residue extracted with boiling heptane. Upon cooling, the ester crystallizes out. It is recrystallized from hexane; MP: 62°–64° C.; yield about 430 mg.

In similar manner there were obtained:
(b) avarol dipropionate
(c) avarol divalerianate
(d) avarol ditrimethylacetate.

EXAMPLE 3

Avarol dicapronate (a) 300 mg of avarol are dissolved in 25 ml of absolute pyridine and 0.6 g of caproic anhydride added in separate portions to the solution while shaking. It is worked up in the customary manner, concentrated to dryness, and the residue extracted with boiling heptane. It is recrystallized from acetone and then from hexane.
Yield: 210 mg.

In similar manner there were obtained:
(b) avarol diisovalerianate
(c) avarol diethylmethylacetate
(d) avarol succinate.

Examples of Pharmaceutical compositions

In the following examples of formulations there can be used as active substance in each case one of the compounds used in accordance with the invention by itself or in mixture with another compound according to the invention.

Example a

| | Tablet Formulation |
|---|---|
| Active substance* | 10 mg |
| Lactose | 18 mg |
| Potato starch | 38 mg |
| Gelatin | 2 mg |
| Talc | 2 mg |
| Magnesium stearate | 0.1 mg |

Example b

| | Tablet Formulation |
|---|---|
| Active substance* | 10 mg |
| Potato starch | 40 mg |
| Polyvinylpyrrolidone | 5 mg |

The tablets are coated with a colored layer of sugar.

Example c

| | Capsule Formulation |
|---|---|
| Active substance* | 10 mg |
| Corn starch | 90 mg |
| Lactose | 50 mg |
| Talc | 2 mg |

This mixture is introduced into gelatin capsules.

Example d

| | Injection Solution |
|---|---|
| Active substance* | 12 mg |
| Sorbitol | 40 mg |
| Sterile water to | 1 ml |

Example e

| | Liquid Oral Formulation |
|---|---|
| Active substance* | 2 g |
| Saccharose | 250 g |
| Glucose | 300 g |
| d-Sorbitol | 150 g |
| Agar-agar | 0.15 g |
| Methylparaben | 0.5 g |
| Propylparaben | 0.05 g |
| Flavoring substance (orange flavor) | 10 g |
| Tartazin yellow | |
| Purified water to | 1000 ml |

Example f

| | Liquid Oral Formulation |
|---|---|
| Active substance* | 2 g |
| Tragacanth | 7 g |
| Glycerin | 50 g |
| Saccharose | 400 g |
| Methylparaben | 0.5 g |
| Propylparaben | 0.05 g |
| Flavoring substance (flavor of black currants) | 10 g |
| Red dye No. 2C.E. 184 | 0.02 g |
| Purified water to | 1000 ml |

Example g

| | Liquid Oral Formulation |
|---|---|
| Active substance* | 2.4 g |
| Saccharose | 400 g |
| Tincture of bitter orange peels | 20 g |
| Tincture of sweet orange peels | 15 g |
| Purified water to | 1000 ml |

The following sections respectively evidence that Avarol is effective in combination with other active compounds or principles; that its employment has no adverse effect upon the immune response of a subject treated therewith; and that an advantageous treatment regimen can be designed because of its extended half-life.

APPLICATION OF AVAROL IN COMBINATION WITH OTHER COMPOUNDS

It is also advantageous to use Avarol in combination with other compounds.

Example

Combination studies were performed in vitro with Avarol together with diethyldithiocarbamate (DDC). DDC has previously been shown to have immunomodulating activity (Lang et al., Lancet 2: 1066; 1985) in AIDS patients and acts by inhibition of superoxide dismutase (SODase) both in vitro and in vivo (Heikkila et al., J. Biol. Chem. 251: 2182-2185; 1976 and Heikkila et al., In: Superoxide and Superoxide Dismutase (eds. A. M. Michelson, J. M. McCord and I. Friedovich), Academic Press, New York; pp. 367-373).

Methods

L5178y mouse lymphoma cells were grown in roller tube cultures in Eagle's minimum essential medium, supplemented with 10% horse serum (Müller et al., Cancer Res. 39: 1102-1107; 1979 and Müller et al. Cancer Res. 45: 4822-4826; 1985). For the dose response experiments, 5 ml cultures were initiated by inoculation of 5000 cells/ml and incubated at 37 degrees C. for 72 hours; the controls had generation times of 10.4-10.6 hours. The cell growth was determined by cell count with a computer supported cell-counter (128-channel counter; Cytocomp, system Michaelis: BIOTRON-Medizinelektronik, Mainz; West Germany). The ED50 ($\pm$SD) was estimated by logit regression (L. Sachs, Angewandte Statistik, Springer-Verlag, Berlin 1984). The mathematical evaluation of the fractional inhibitory concentration indices (FIC indices) of Avarol-/Avarone-DDC combinations was performed according to published equations and experimental conditions (Müller et al., Cancer Lett. 1: 127-132; 1976; and Phillips et al., Antimicrob. Agents Chemother. 9: 736-740, 1976). $FIC>1$ are interpreted as antagonistic; $FIC=1$ as additive effects; $FIC<1$ as suggestive of synergism; and $FIC<0.5$ as significant synergism.

Results

In this set of experiments, L5178y cells were incubated with Avarol in the absence or presence of the established SODase inhibitor DDC. In the absence of DDC, the ED50 for avarol was determined to be $0.94\pm0.14$ $\mu$M, as described previously (Müller et al., Cancer Res. 45: 4822-4826; 1985).

Coaddition of DDC at the concentrations of 1.46 $\mu$M or 1.71 $\mu$M to the cultures, significantly lowered the ED50 concentrations to $0.27\pm0.04$ $\mu$M and $0.108\pm0.015$ $\mu$M. The two DDC concentrations chosen caused an inhibition of cell growth by 26 and 38% respectively in the absence of Avarol.

As a further proof for the additive effect of Avarol in combination with DDC, the FIC indices were determined.

Concentration ratios between 0.2:1 to 1.3:1.0 (Avarol:DDC) were chosen. The calculated FIC indices varied between 0.82 and 1.04 indicating an additive interaction between Avarol and DDC (Table).

Conclusion

These studies show that Avarol can be administered in vitro in combination with other therapeutic agents resulting in a beneficial therapeutical effect.

Table

Fractional inhibitory concentration indices (FIC indices) for avarol-DDC combination on L5178y cells The standard incubation conditions (5 ml and 72 hours) were chosen. The combination ratios are based on $X\mu$M avarol to y $\mu$M DDC.

| Drug combination | Concentration ratio | FIC index |
|---|---|---|
| Avarol:DDC | 0.3:1.0 | 0.87 |
| | 0.5:1.0 | 0.82 |
| | 1.3:1.0 | 0.90 |

INFLUENCE OF AVAROL ON SELECTED IMMUNE RESPONSES IN VITRO AND IN VIVO

In vitro studies

Previous studies revealed that T-cell derived leukemia cells are more sensitively inhibited by avarol than normal T- or B-lymphocytes (Müller et al., Cancer Res. 45: 4822–4826; 1985 and Müller et al., Eur. J. Cancer Clin. Oncol. 22: 473–476; 1986). The lymphoma cell growth is inhibited by 50% within the concentration range 0.3–0.4 μg/ml (=0.9–1.1 μM), while the [$^3$H] dThd-incorporation rate in normal T-lymphocytes is inhibited by 50% between 0.5–1.3 μg/ml and, in normal B-lymphocytes, between 1.6–1.9 μg/ml. Therefore the following in vitro studies were performed with 0.5–3 μg/ml of avarol.

In vivo studies

From previous experiments with NMRI mice, bearing L5178y cells, it is known that the chemotherapeutical dose of avarol is in the range of 1–50 mg/kg at a 50% lethal dose of 269.1 mg/kg (Müller et al., Cancer Res. 45: 4822–4826; 1985). The 50% lethal dose (treatment for 5 days) for male Sprague-Dawley rats was determined to be 235.7 mg/kg. Therefore, daily doses of avarol of 1–30 mg/kg/injection were chosen for the following in vivo studies.

Rationale

Considering an application of avarol in the treatment of acquired immunodeficiency syndrome [AIDS] patients, the effect of avarol on immune responses was studied in vitro and in vivo. The results demonstrate that avarol causes, at antileukemic doses in vivo, no influence on delayed-type hypersensitivity (DTH) and on antibody-mediated hypersensitivity (AMH) but displays a stimulatory effect on antibody production both in vitro and in vivo. These properties are very advantageous, because AIDS patients show both B- and T-cell deficiencies (Ammann et al., J. Amer. Med. Ass. 251: 1447–1449; 1984).

1. In vitro immunoglobulin (Ig) production

Method

Human peripheral blood lymphocytes ($6 \times 10^5$ cells/ml) were cultured in the presence of 0 to 2 μg/ml of pokeweed mitogen (PWM; Sigma no. 9379) in Dulbeccos minimum essential medium, supplemented with 20% fetal calf serum, for 6 days. The assays were performed in a final volume of 200 μl in microtiter plates (Dynatech; M129B) (Müller et al., Eur. J. Cancer Clin. Oncol. 22: 473–476; 1986). Avarol in a concentration range of 0–3 μg/ml was added at time 0 or 3 days after starting the culture. The supernatants were harvested and assayed for human immunoglobulin content.

The culture supernatants were assayed by the enzyme-linked immunosorbent assay (Houtman et al., Clin. Exp. Immunol. 62: 696–704; 1985) using anti-human IgG (Dakopatts, Hamburg; P214) and anti-human IgM (Dakopatts; P215). These antibodies were conjugated to peroxidase. Bound enzyme activity was measured using 2,2'-azino-bis(3-ethylbenzthiazolinesulfonic acid) (Sigma no. A-1888) as substrate.

Results

Under the assay conditions used, human peripheral blood lymphocytes (unseparated) produced 1.3 μg/ml of IgG and 8.9 μg/ml of IgM during a 6-day culture (Table 1). The production was enhanced upon addition of PWM to 4.1 μg/ml (IgG) and 12.3 μg/ml (IgM). I used a PWM concentration of only 2 μg/ml, which was previously found to be suboptimal, in order to detect more sensitively a possible Ig production after avarol treatment. The results revealed a significant increase of both IgG and IgM production in cultures treated with 0.3 or 1 μg/ml of avarol, irrespectively of the presence of PWM (Table 1) and of the time period for avarol presence (0 to 6 days or 3 to 6 days). At higher avarol concentrations, the Ig production turned to normal values.

2. In vivo immunoglobulin (Ig) production

Concerning the functional consequences of the compound onto B-cells in vitro, I found (previous section) that both the IgG and the IgM secretion is stimulated in cultures of human lymphoid cells (unseparated) which are treated with non-cytostatic concentrations of avarol. This finding is supported by the results of the Jerne plaque test. The experiments revealed that single-cell suspensions prepared from the spleens of mice, immunized with sheep red blood cells (SRBC), that had been pretreated with therapeutical doses of avarol, contained a higher number of plaque-forming cells than the spleens from untreated animals.

Method

The plaque test of Jerne and Nordin (Science 140: 405–406, 1963) was used with the modification given by Cunningham and Szenberg (Immunolog. 14: 599–601; 1968). Briefly, 8 male NMRI mice per group (20–22 g) were immunized on day 0 by i.p. injection of $5 \times 10^8$ SRBC in 0.5 ml saline. Treatment with avarol was done i.p. either from day 0 to day +4 or from day −4 to day 0. One hour after the last drug administration, the animals were killed by a blow on the head and bled. The spleens were removed and a single cell suspension was prepared by teasing the pooled spleens through a 120-μm mesh sieve. After lysing the erythrocytes by 0.15M $NH_4Cl$, the cells were washed twice in Hank's balanced salt solution containing 29 ml of 7.5% $NaHCO_3$ and 10 ml of 1M HEPES buffer solution per one liter. The cells were resuspended in 2 ml per spleen. Six Cunningham chambers per group were filled with a mixture of 0.5 ml of a suitable dilution of spleen cells (generally 1:100), 0.5 ml of a suspension of SRBC ($10^9$/ml) and 125 μl of normal guinea pig complement. After 90–120 min of incubation at 37° C., the number of plaques was counted. Plaques per spleen or per $10^6$ spleen cells were calculated.

The pooled blood of 8 mice was centrifuged to obtain the serum. IgM and IgG titers were measured with the mercaptoethanol method (Hudson, L. and Hay, F. C. Practical Immunology, Blackwell Sci., Oxford; 1983).

Results

Applying the modified Jerne assay the number of plaque forming cells in spleen of mice, injected with SRBC, was determined in the absence or presence of avarol treatment (Table 2). Animals, treated with 30 mg/kg of avarol from day 0 to day +4, had a 28% higher number of plaque forming cells/spleen, and those treated from day −4 to day 0, a 21% increase.

3. Delayed-type hypersensitivity (DTH)

Method

Reaction to sheep red blood cells (SRBC)

DTH was produced according to the method of Lagrange et al. (J. Exp. Med. 139: 528–542; 1974) and Liew (Eur. J. Immunol. 7, 714–718; 1977). Male NMRI mice (20–23 g, 10 animals/group) were immunized with $10^8$ SRBC/40 μl into one foot pad (day 0). Four days later $10^9$ SRBC/40 μl were injected into the other foot pad. After 24 hours, paw size was measured with a dial gauge caliper Odi-Test OOT (H. C. Kroeplin, Schlüchtern, Germany). Avarol (in 0.15% [w/v] methylcellulose) was administered daily i.p. either from day −2 to +1 or from day +2 to +4. The level of DTH was expressed as foot pad increase, determined after 24 hrs; and it is given in mm. Non-treated groups were injected i.p. with methylcellulose only. Treated groups were compared with the controls using the U-test of Wilcoxon et al. (Sachs, L. Angewandte Statistik, Springer-Verlag, Berlin; 1984).

Contact allergy to oxazolone

Allergic contact dermatitis against oxazolone was produced according to the method of Asherson and Ptak (Immunol. 15: 405–416; 1968) as well as those of Bure and Degrand (Agents and Actions 9: 534; 1979). Male NMRI mice (20–22 g; 10/group) were sensitized with 100 μl of a 2% oxazolone in acetone solution onto the shaved abdomen (day 0). Animals were treated with avarol (i.p.) daily from day −1 to +2 or from day +6 to +8; control group was treated with deoxymethasone (Casella-Hoechst) as a standard per os at a daily dose of 30 mg/kg for the same period of time as for avarol. Seven days after sensitization 10 μl of a 3% oxazolane (this concentration was previously found to give more reproducible results than the lower 2% concentration) solution were topically applied onto the inner side of one ear, whereas the other ear received only acetone. Twenty-four hours later the animals were killed and two 8 mm (diameter) pieces were punched out of both ears. The weight differences were recorded. Treated groups were compared with controls using the U-test.

Results

The effect of avarol on cell-mediated, or delayed type hypersensitivity, reaction in mice was determined in two ways; (i) reaction to sheet red blood cells and (ii) reaction to oxazolone sensitization.

Delayed-type hypersensitivity (DTH) to sheep red blood cells (SRBC): Avarol was administered at three different doses and during two different time periods as described under "Methods". Given during the period −2 to +1 (with respect to the last SRBC administration), avarol caused no significant immunosuppressive influence on DTH to SRBC in NMRI mice up to daily doses of 30 mg/kg. However, when given on day +2 to +4 after immunization, avarol administration at doses higher than 10 mg/kg resulted in a weak but significant immunosuppressive effect.

Contact allergy to oxazolone: In a second approach, the mice were topically sensitized with oxazolone and challenged again after 7 days with the same irritant. Avarol or deoxymethasone (=negative control) were administered from day −1 to +2 or from day +6 to +8 with respect to the day of sensitization, as described under "Methods". Deoxymethasone caused a significant immunosuppressive influence on DTH reaction (24 hours increase in ear thickness [in mg] if treated from day −1 to +2: 10.2±6.0, or 10.9±6.1 at a treatment from day +6 to to +8; the corresponding controls are 22.3±5.6 and 18.5±3.7, respectively). On the other hand, avarol in a dose range from 3–30 mg/kg either from day −1 to +2 or day +6 to +8 did not influence significantly P>0.05) the DTH oxazolone.

4. Antibody mediated hypersensitivity (AMH)

Method

A modified active Arthus reaction was performed as described (Titus et al., J. Immunol. Methods 45: 65–78; 1981). Male Sprague-Dawley rats (8/group) weighing 120 g were immunized by injecting into the tail base 0.5 ml of a suspension of 4.4 ml pertussis vaccine (Behringwerke, Marburg) in 65.6 ml of 0.9% saline plus 0.7 g ovalbumin (3×cryst.) in 100 ml paraffin oil. Three weeks after immunization 0.1 ml of 0.03% ovalbumin solution were injected into a hind paw and the paw volume was measured with a water plethysmometer (Rhema) immediately thereafter and again after 4 hours. The animals were treated i.p. with daily doses from 3–30 mg/kg of avarol (in 0.15% [w/v] methylcellulose) according to the following schedules: (i) day −1 to +2, (ii) day +18 to +21 or (iii) twice 24 hours and 30 minutes before challenge (day 0 represents the day of immunization). The controls received methylcellulose only. Values are compared with a control group using Student's-t-test (L. Sachs. Angewandte Statistik, Springer-Verlag, Berlin; 1984).

Results

I used a modified Arthus reaction to determine the possible influence of avarol on the AMH in rats, caused by ovalbumin. The results revealed no significant suppression of the Arthus reaction by avarol, irrespectively of the following schedules chosen; (i) day −1 to +2 or (ii) day +18 to +21, related to day 0 of immunization or (iii) if applied immediately before the challenge with ovalbumin. This weak suppression of the reaction, observed when rats were treated with avarol (30 mg/kg) 24 hours and 30 minutes before challenge, was also found to be not significant (P>0.05).

In Summary

The effect of avarol on the lymphoid system was studied both in vitro and in vivo. Avarol increased significantly the IgG and IgM production by cultures of human lymphoid cells (unseparated) in vitro and slightly the number of plaque forming cells in vivo in spleen of mice. Moreover, a pretreatment of mice with the avarol resulted in a higher [$^3$H]-dThd incorporation rate in both macrophage-containing and macrophage-depleted lymphocyte cultures in vitro. The stimulatory influence of avarol on humoral immune responses is not accompanied by a change of the antibody-mediated hypersensitivity reaction, as measured by the Arthus reaction. No significant influence of avarol on the cellular immune system in vivo (rats or mice) was found, as taken from studies on delayed-type hypersensitivity reactions to sheep red blood cells and to oxazolone. The in vitro and animal data indicate that avarol combines useful properties, e.g. anti-HIV efficience in vitro and augmentation of humural immune responses.

Table 1

Mean immunoglobulin production in cultures of peripheral human blood lymphocytes in dependence on the mitogenic effect of PWM and on avarol

| Avarol concentration (μg/ml) | PWM | Immunoglobulin synthesized (μg/ml) | | | |
|---|---|---|---|---|---|
| | | IgG time (days) | | IgM time (days) | |
| | | 0 to 6 | 3 to 6 | 0 to 6 | 3 to 6 |
| 0 | − | 1.3 ± 0.3 | 1.4 ± 0.3 | 8.9 ± 2.0 | 8.5 ± 1.8 |
| | + | 4.1 ± 0.7 | 4.0 ± 0.8 | 12.3 ± 2.6 | 11.7 ± 2.2 |
| 0.3 | − | 2.1 ± 0.5+ | 2.0 ± 0.5+ | 14.7 ± 3.4+ | 14.2 + 3.3+ |
| | + | 6.7 ± 1.5+ | 7.9 ± 1.9++ | 20.4 ± 5.1+ | 24.7 ± 5.6++ |
| 1.0 | − | 2.3 ± 0.6+ | 2.2 ± 0.5+ | 15.6 ± 4.0+ | 15.9 ± 4.2++ |
| | + | 7.0 ± 1.6+ | 8.5 ± 1.9++ | 23.5 ± 5.5++ | 25.6 ± 5.9++ |
| 3.0 | − | 1.2 ± 0.3 | 1.3 ± 0.3 | 8.1 ± 1.8 | 8.4 ± 1.9 |
| | + | 3.9 ± 1.0 | 4.9 ± 1.0 | 10.5 ± 2.6 | 11.7 ± 2.9 |

+$P < 0.01$; ++$P < 0.005$

Table 2
Effect of avarol on the number of plaque forming cells in the spleen of mice

| Avarol (mg/kg) | Schedule (days) | Cells/ spleen ($\times 10^{-7}$) | Plaque forming cells per: | | Titer | |
|---|---|---|---|---|---|---|
| | | | spleen ($\times 10^{-5}$) | $10^6$ cells | IgM | IgG |
| 0 | from 0 to +4 | 11.3 | 3.13 | 2,782 | 256 | 4 |
| | from −4 to 0 | 11.6 | 2.62 | 2,259 | 512 | 4 |
| 30 | from 0 to +4 | 12.0 | 3.98 | 3,316 | 256 | 2 |
| | from −4 to 0 | 14.4 | 3.18 | 2,202 | 512 | 4 |

DETERMINATION OF THE HALF-LIFE OF TRITIUM-LABELLED AVAROL AND OF THE ORGAN DISTRIBUTION IN RATS

Animals: Sprague-Dawley rats (male).

Half-life

Avarol was injected (intravenously) at therapeutic doses into rats. The following concentrations of Avarol were chosen: 2 mg/kg, 10 mg/kg, and 20 mg/kg. Tritium labelled Avarol was obtained by converting Avarol into Dihydro-avarol in the presence of tritium gas.

| Doses of Avarol | Percentage of Radioactivity in Blood (100% is set as the amount of radioactivity present 10 minutes after termination of i.v. injection) Time of Determination (hours after termination of i.v. injection) | | | | |
|---|---|---|---|---|---|
| | 1 | 6 | 12 | 24 | 48 |
| 2 mg/kg | 95 | 91 | 73 | 41 | 23 |
| 10 mg/kg | 96 | 88 | 72 | 43 | 26 |
| 20 mg/kg | 92 | 83 | 75 | 39 | 21 |

From these determinations it is evident that the half-life of Avarol in rats is approximately 22 hours.

Organ Distribution

The organ distribution was determined by the same method using tritium labelled Avarol. The determinations were performed 24 hours after termination of the i.v. application.

| Organ | Doses of Avarol (mg/kg) | Concentration of Avarol (microgram of Avarol per gram of tissue) |
|---|---|---|
| Blood | 2 | 4.3 |
| | 10 | 5.2 |
| | 20 | 5.8 |
| Spleen | 2 | 1.7 |
| | 10 | 1.9 |
| | 20 | 2.2 |
| Liver | 2 | 6.4 |
| | 10 | 6.9 |
| | 20 | 7.4 |
| Kidney | 2 | 1.6 |
| | 10 | 2.2 |
| | 20 | 2.4 |
| Heart | 2 | 0.7 |
| | 10 | 0.9 |
| | 20 | 0.9 |
| Testes | 2 | 0.48 |
| | 10 | 0.63 |
| | 20 | 0.67 |
| Brain | 2 | 0.45 |
| | 10 | 0.58 |
| | 20 | 0.64 |
| Skin | 2 | 0.4 |
| | 10 | 0.6 |
| | 20 | 0.6 |

These concentrations were determined on the basis of radioactivity. Moreover, the chemical nature of the radioactive product was identified by high-pressure liquid chromatography and found to consist of over 90% of Avarol. In addition, the biological activity of the compound in the blood was determined after extraction with ethyl acetate and estimated in the L5178y cell system in vitro (Müller, W.E.G. et al.; Comp. Biochem. Physiol. 80C, 47-52; 1985). Using this system, the biological activity of the compound, present in the blood, was determined and converted on a gram basis. Using this approach the concentration in the blood was only 5–15% lower than that determined on the basis of radioactivity.

Conclusion (1) Avarol undergoes only a slight modification to a biologically-inactive form (not more than 15%) after circulation in the body for 22 hours.

(2) Avarol has a long half-life (approximately 22 hours) after i. v. administration of anti-tumor concentrations.

(3) Avarol penetrates the blood-brain barrier.

These properties of Avarol in the body of rats appear to be highly favorable for an in vivo application of Avarol in man. On the basis of these data it is deduced that, for the therapeutic application of Avarol in man, only 1-2 injections are needed per day to warrant beneficial therapeutical doses which are in the range of 0.3 to 5 microgram/ml of blood.

Rationale: Interferon-Gamma Production Stimulation

Interferon-gamma is a mediator of T-lymphocyte immunity and is probably the key-cell derived lymphokine that induces macrophages and other potential host defense cells to exert enhanced antimicrobial activity against both intracellular and extracellular pathogens. It is established that patients with AIDS and AIDS-related complex show an impaired gamma Interferon production (H. W. Murray et al.; The New England Journal of Medicine 313; 1504–1510, 1985). The molecular reason for this manifestation is a profound impairment of antigen-induced Interleukin-2 secretion (H. W. Murray; J. Clin. Invest 76: 1959–1964; 1985). Under normal conditions in vivo, Interferon gamma is produced by T-lymphocytes, which have to be stimulated by Interleukin-2. Antigens from viruses such as vaccinia or herpes simplex can trigger Interferon gamma secretion in leukocytes from immunized humans.

It is therefore advantageous that an anti-AIDS chemotherapeutic agent is provided with the ability to induce gamma Interferon in T-lymphocytes. Avarol is such a compound which combines both anti-AIDS activity with the ability to induce Interferon gamma production. The experiments were performed in vitro, using peripheral human lymphocytes (buffy coat cells) in culture.

Materials and Methods

Effector cells

Buffy coat cells were prepared by centrifugation on Ficoll-Plaque gradient and washed two times. Subsequently the cells were divided and adjusted to a concentration of $5 \times 1,000,000$ cells/ml.

Interferon measurement

Levels of Interferon were defined by an Enzymeimmunoassay (EIA). Interferon gamma: 96 well flat bottom plates (Greiner, Neurtingen) were coated with a monoclonal antibody recognizing Interferon gamma. 200 µl of the supernatant sample were added per well together with Interferon gamma-peroxidase coupled (50 µl), consisting of the same antibody as used for coating. After 24 hours of incubation the plates were washed with buffered salt solution containing 0.5% w/v Tween 20. The enzymatic reaction is completed by a preparation containing hydrogen peroxide substrate. The reaction is stopped within 15 minutes by 100 µl of sulfuric acid per well. The amount of Interferon is defined by comparing the extinction of the test sample with a standard curve produced by known values of Interferon gamma.

Interferon

Interferon gamma was purchased from Hoffmann-La Roche, Grenzach, Germany.

Results

Buffy coat cells were incubated with different Avarol concentrations for 0-96 hours. The results are summarized as follows:

| Avarol concentration (µg/ml) | Titer of Interferon-gamma produced by lymphocytes (Units/ml of supernatant) Incubation period (hours) | | | | |
|---|---|---|---|---|---|
| | 0 | 24 | 48 | 72 | 96 |
| 0 | 2 | 5 | 3 | 7 | 4 |
| 0.2 | 4 | 17 | 24 | 26 | 21 |
| 0.5 | 4 | 23 | 74 | 89 | 118 |
| 1.0 | 3 | 20 | 52 | 62 | 73 |

(The results are means of four parallel experiments; the standard deviations are less than 10%)

From these data, it is evident that Avarol induces significant and pronounced Interferon gamma in vitro at an optimal dose of 0.5 µg/ml.

Conclusion

Avarol has an additional beneficial therapeutic effect: The here-presented in vitro studies show that Avarol induces Interferon gamma production in vitro and suggests that it acts also in vivo in the same manner in AIDS patients.

In conclusion, from the foregoing, it is apparent that the present invention provides a novel method for the treatment and control of AIDS and ARC using Avarol and derivatives and/or precursors and/or prodrugs thereof, and pharmaceutical compositions embodying these active ingredients for the said intended use, all having the foregoing enumerated characteristics and advantages.

It is to be understood that the invention is not to be limited to the exact details of operation, or to the exact compositions, methods, procedures or embodiments shown and described, as obvious modifications and equivalents will be apparent to one skilled in the art, and the invention is therefore to be limited only by the full scope which can be legally accorded to the appended claims.

I claim:

1. A method of treating AIDS/ARC comprising the step of administering an effective anti-AIDS/ARC amount of avarol or 3,4-dihydroavarol to a living animal body in need of said treatment.

2. The method of claim 1, wherein the living animal body is a human being.

* * * * *

UNITED STATES PATENT AND TRADEMARK OFFICE
CERTIFICATE OF CORRECTION

PATENT NO. : 4,939,177

DATED : July 3, 1990

INVENTOR(S) : Werner E. G. Müller

It is certified that error appears in the above-identified patent and that said Letters Patent is hereby corrected as shown below:

Column 5, line 66; "0.01" should read -- 0.1 --.

Column 7, after the formulas, (approximately line 18) insert
-- Molecular Formula of Avarol
$C_{21}H_{30}O_2$; Mol wt: 314.22
C 80.32%; H 9.81%; O 9.87%
and the 3,4-dihydro derivatives thereof. --

Column 13, line 42; "sheet" should read -- sheep --.

Signed and Sealed this

Twenty-fourth Day of September, 1991

Attest:

HARRY F. MANBECK, JR.

Attesting Officer

Commissioner of Patents and Trademarks